(12) United States Patent
Nakahara et al.

(10) Patent No.: US 10,131,603 B2
(45) Date of Patent: Nov. 20, 2018

(54) METHOD FOR REDUCING METAL OF SUGAR-ALCOHOL COMPOUND AND SUGAR-ALCOHOL COMPOUND

(71) Applicant: SHIN-ETSU CHEMICAL CO., LTD., Tokyo (JP)

(72) Inventors: Takayoshi Nakahara, Jyoetsu (JP); Takeru Watanabe, Jyoetsu (JP); Seiichiro Tachibana, Jyoetsu (JP); Tsutomu Ogihara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/585,720

(22) Filed: May 3, 2017

(65) Prior Publication Data
US 2017/0369407 A1 Dec. 28, 2017

(30) Foreign Application Priority Data
Jun. 23, 2016 (JP) ................................ 2016-124209

(51) Int. Cl.
*C07C 27/26* (2006.01)
*C07C 29/92* (2006.01)
*C07C 31/26* (2006.01)

(52) U.S. Cl.
CPC .............. *C07C 29/92* (2013.01); *C07C 31/26* (2013.01)

(58) Field of Classification Search
None
See application file for complete search history.

(56) References Cited

U.S. PATENT DOCUMENTS

| 4,172,195 A | * | 10/1979 | Koster | C07H 1/06 536/17.1 |
| 5,126,267 A | * | 6/1992 | Boaz | C07B 57/00 435/130 |
| 2015/0004791 A1 | | 1/2015 | Ogihara et al. | |

FOREIGN PATENT DOCUMENTS

| JP | H07-028254 A | 1/1995 |
| JP | 2007-017950 A | 1/2007 |
| JP | 2015-028145 A | 2/2015 |
| JP | 2016-079169 A | 5/2016 |

OTHER PUBLICATIONS

Wen et al. J. Chem Technol Biotechnol 79:403-406.*
B. B. Bahule et al., "Protection of Diol as Acetonide Using Acetone and Cation Exchange Resin as a Catalyst," IOSR Journal of Applied Chemistry, vol. 3, Issue 1, 2012, pp. 28-29.
May 30, 2018 Office Action issued in Korean Application No. 10-2017-0075663.

* cited by examiner

*Primary Examiner* — Ana Z Muresan
(74) *Attorney, Agent, or Firm* — Oliff PLC

(57) ABSTRACT

The present invention provides a method for reducing a metal of a sugar-alcohol compound, the method including the steps of (A) protecting a hydroxyl group of a sugar-alcohol compound containing metal impurities with a protecting group, (B) removing the metal impurities from the sugar-alcohol compound having the hydroxyl group protected with the protecting group, and (C) eliminating the protecting group of the sugar-alcohol compound from which the metal has been removed. There can be provided a method for reducing a metal of a sugar-alcohol compound that can provide a sugar-alcohol compound with a suitable quality for the semiconductor apparatus manufacturing process.

12 Claims, No Drawings

METHOD FOR REDUCING METAL OF SUGAR-ALCOHOL COMPOUND AND SUGAR-ALCOHOL COMPOUND

BACKGROUND OF THE INVENTION

Field of the Invention

The present invention relates to a method for reducing a metal of a sugar-alcohol compound to be used in, for example, a resist underlayer film composition and to a sugar-alcohol compound.

Description of the Related Art

A sugar-alcohol compound is useful and can be used in various semiconductor apparatus manufacturing processes. For example, it is proposed to apply this compound to a resist removing liquid or a resist underlayer film composition for multilayer resist process (for example, Patent Documents 1 to 3). However, a commercially available sugar-alcohol compound has high metal content and is difficult to reduce a metal by a usual purification method such as recrystallization. Thus, such a compound can cause defects such as short circuit and wire disconnection when used in a semiconductor apparatus manufacturing process which is significantly affected by metal impurities, and has difficulty in practical use. Therefore, an industrial method for reducing a metal of a sugar-alcohol compound is required.

PRIOR ART DOCUMENTS

Patent Documents

Patent Document 1: Japanese Unexamined Patent publication (Kokai) No. H07-28254
Patent Document 2: Japanese Unexamined Patent publication (Kokai) No. 2007-17950
Patent Document 3: Japanese Unexamined Patent publication (Kokai) No. 2015-28145

SUMMARY OF THE INVENTION

The present invention was accomplished in view of the above-described circumstances. It is an object of the present invention to provide a method for reducing a metal of a sugar-alcohol compound that can provide a sugar-alcohol compound with a suitable quality for the semiconductor apparatus manufacturing process, and a sugar-alcohol compound in which a metal is reduced.

To achieve this object, the present invention provides a method for reducing a metal of a sugar-alcohol compound, the method comprising the steps of:

(A) protecting a hydroxyl group of a sugar-alcohol compound containing metal impurities with a protecting group;

(B) removing the metal impurities from the sugar-alcohol compound having the hydroxyl group protected with the protecting group; and (C) eliminating the protecting group of the sugar-alcohol compound from which the metal has been removed.

This method for reducing a metal of a sugar-alcohol compound can provide a sugar-alcohol compound with a suitable quality for the semiconductor apparatus manufacturing process.

In this method, the sugar-alcohol compound containing metal impurities preferably includes any of erythritol, threitol, arabinitol, xylitol, ribitol, iditol, galactitol, sorbitol, mannitol, volemitol, perseitol, octitol, inositol, and quercitol.

The inventive method for reducing a metal of a sugar-alcohol compound is suitable for reducing the metal content of such compounds.

Additionally, the step (B) preferably includes (B1) liquid-liquid separation and water washing or (B2) distillation.

In the inventive method for reducing a metal of a sugar-alcohol compound, since a hydroxyl group of the sugar-alcohol compound containing metal impurities is protected with a protecting group in the step (A), liquid-liquid separation and water washing or distillation can be employed in the step (B).

The protecting group is preferably acetonide.

Acetonide can provide a final product with low cost, easy industrialization, and high purity. Thus, acetonide is particularly preferable as the protecting group.

Additionally, the step (C) is preferably performed by hydrolysis reaction or alcoholysis reaction.

When the step (C) is performed by hydrolysis reaction or alcoholysis reaction, deprotection can be carried out while preventing metal impurity contamination.

Furthermore, the present invention provides a sugar-alcohol compound having a sodium impurity content of 100 ppb or less.

Such a sugar-alcohol compound, in which a metal is reduced, can be suitably used in the semiconductor apparatus manufacturing process.

The inventive method for reducing a metal of a sugar-alcohol compound can easily provide a large amount of a sugar-alcohol compound in which a metal is reduced to a suitable amount for the semiconductor apparatus manufacturing process. Thus, this method is significantly industrially valuable.

Moreover, the inventive sugar-alcohol compound, in which a metal is reduced, can be suitably used in the semiconductor apparatus manufacturing process.

DETAILED DESCRIPTION OF THE PREFERRED EMBODIMENTS

As mentioned above, the application of a sugar-alcohol compound to the semiconductor apparatus manufacturing process is proposed. On the other hand, a material used in the semiconductor apparatus manufacturing process requires reducing the metal content such that every metal is controlled to be at least 100 ppb or less, preferably 50 ppb or less. In general, a commercially available sugar-alcohol compound has high metal content, especially a sodium content of 1,000 ppb or more, and requires some metal reducing treatment for the application to an electronic material. The metal reducing treatment generally used is liquid-liquid separation and water washing, distillation, recrystallization, etc. However, since the sugar-alcohol compound is a solid that has high water-solubility and high melting point, the liquid-liquid separation and water washing and the massive distillation are almost impossible. Regarding the recrystallization, although the treatment itself is possible, the metal reducing effect is insufficient. A possible alternative method is to treat a solution of the compound with a commercially available metal removing filter, ion exchange resin, or the like. However, this method often causes malfunction in the application due to elution of impurities from the filter or the resin and thus is unsuited for the case. In view of the above problems, it is desired to develop a method for reducing a metal of a sugar-alcohol compound that can provide a sugar-alcohol compound with a suitable quality for the semiconductor apparatus manufacturing process.

The present inventors have earnestly studied on the method for reducing a metal of a sugar-alcohol compound and consequently found that the above object can be accomplished by the method for reducing a metal of a sugar-alcohol compound, including the steps of: (A) protecting a hydroxyl group of a sugar-alcohol compound containing metal impurities with a protecting group; (B) removing the metal impurities from the sugar-alcohol compound having the hydroxyl group protected with the protecting group; and (C) eliminating the protecting group of the sugar-alcohol compound from which the metal has been removed, thereby bringing the present invention to completion.

Hereinafter, embodiments of the present invention will be described in detail, but the present invention is not limited thereto.

[Sugar-Alcohol Compound]

The inventive sugar-alcohol compound has a sodium impurity content of 100 ppb or less, preferably 50 ppb or less. In particular, the inventive sugar-alcohol compound preferably has a solid content of every metal impurity including sodium of 100 ppb or less.

Illustrative examples of the sugar-alcohol compound include erythritol, threitol, arabinitol, xylitol, ribitol, iditol, galactitol, sorbitol, mannitol, volemitol, perseitol, octitol, inositol, and quercitol, although the compound is not particularly limited thereto.

Such a sugar-alcohol compound of the present invention, in which a metal is reduced, can be suitably used in the semiconductor apparatus manufacturing process or the like.

(Method for Reducing Metal of Sugar-Alcohol Compound)

The inventive method for reducing a metal of a sugar-alcohol compound includes the steps of: (A) protecting a hydroxyl group of a sugar-alcohol compound containing metal impurities with a protecting group; (B) removing the metal impurities from the sugar-alcohol compound having the hydroxyl group protected with the protecting group; and (C) eliminating the protecting group of the sugar-alcohol compound from which the metal has been removed.

<Step (A)>

According to the present invention, first, in a protecting step, a hydroxyl group of a sugar-alcohol compound containing metal impurities (hereinafter, also referred to as a metal reduction target sugar-alcohol compound) is protected with a protecting group (step (A)).

The sugar-alcohol compound containing metal impurities preferably includes, for example, any of erythritol, threitol, arabinitol, xylitol, ribitol, iditol, galactitol, sorbitol, mannitol, volemitol, perseitol, octitol, inositol, and quercitol, although the compound is not particularly limited thereto.

The protecting group used for protecting the hydroxyl group in the step (A) is not particularly limited and may be appropriately selected from usual ether protecting groups, ester protecting groups, acetal protecting groups, silyl ether protecting groups, and carbonate protecting groups. Illustrative examples of the usable protecting group include ether protecting groups such as a t-butyl group and a benzyl group; ester protecting groups such as a formyl group, an acetyl group, a pivaloyl group, a benzoyl group, and a trifluoroacetyl group; acetal protecting groups such as a methoxymethyl group, a 2-methoxyethoxymethyl group, a tetrahydropyranyl group, a 1-ethoxyethyl group, a methylene group, an ethylidene group, acetonide (an isopropylidene group), and a benzylidene group; silyl ether protecting groups such as a trimethylsilyl group, a triethylsilyl group, a triisopropylsilyl group, and a t-butyldimethylsilyl group; and carbonate protecting groups such as methoxycarbonyl, t-butoxycarbonyl, benzyloxycarbonyl, and cyclic carbonate, although not limited thereto. Among them, acetonide can provide a final product with low cost, easy industrialization, and high purity, and thus is particularly preferably used. In addition, the protection of the hydroxyl group may be performed on a part of hydroxyl groups or all of hydroxyl groups contained in the metal reduction target sugar-alcohol compound. Preferably, 50% or more of hydroxyl groups are protected.

Hereinafter, the case of using acetonide for protection (acetonide protecting reaction) in the step (A) will be described in detail, but the present invention is not limited thereto. The acetonide protecting reaction is generally performed by using an acetone equivalent and an acid catalyst and can be shown by the following partial formula. The group shown by the following partial formula (1) is a part of hydroxyl groups contained in the metal reduction target sugar-alcohol compound. The group shown by the partial formula (1) is protected with acetonide and changes into the group shown by the following partial formula (2) by reaction of the metal reduction target sugar-alcohol compound with the acetone equivalent in the presence of the acid catalyst in a solvent or without a solvent. In this manner, a sugar-alcohol compound having the hydroxyl group protected with acetonide (an acetonide protector) is obtained.

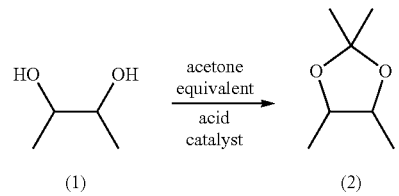

wherein the dotted line represents a bond.

The acid catalyst may be selected from, for example, mineral acids such as sulfuric acid, hydrochloric acid, phosphoric acid, perchloric acid, and hydrobromic acid; Lewis acids such as boron trifluoride, boron trifluoride diethyl ether complex, dibutyltin oxide, aluminum chloride, zinc chloride, titanium tetrachloride, and titanium tetramethoxide; sulfonic acids such as methanesulfonic acid and p-toluenesulfonic acid; salts such as potassium hydrogen sulfate, calcium chloride, magnesium chloride, and pyridinium p-toluenesulfonate; carboxylic acids such as oxalic acid and trifluoroacetic acid; and acidic resins such as a cation exchange resin, solely or in combination, depending on reaction conditions. The amount of the acid catalyst to be used is preferably 0.0001 to 10 mol, particularly 0.001 to 5 mol, per 1 mol of the metal reduction target sugar-alcohol compound.

The acetone equivalent may be selected from, for example, acetone, 2,2-dimethoxypropane, 2,2-diethoxypropane, 2-methoxypropene, and 2-ethoxypropene, solely or in combination, depending on reaction conditions. The amount of the acetone equivalent to be used is preferably 0.2 to 100 mol, particularly 0.5 to 50 mol, per 1 mol of hydroxyl groups in the metal reduction target sugar-alcohol compound.

When the reaction is performed in a solvent, the reaction solvent may be selected from, for example, hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform, and 1,2-dichloroethane;

non-protic polar solvents such as N,N-dimethylformamide, N,N-dimethylacetamide, dimethylsulfoxide, and N-methylpyrrolidone; esters such as ethyl acetate and butyl acetate; ketones such as acetone and 2-butanone; and nitriles such as acetonitrile, solely or in combination, depending on reaction conditions. The reaction temperature is preferably selected in the range of 0° C. to the reflux temperature of the solvent, depending on the reaction rate.

In view of yield, the reaction is desirably performed until the reaction rate is no longer changed on trace of the reaction by gas chromatography (GC), liquid chromatography (LC), thin layer chromatography (TLC), or the like; in general, the reaction time is about 0.5 to 24 hours. The reaction can be terminated by adding a base to neutralize the acid catalyst or by water washing or filtration to remove the acid catalyst. The base added for neutralization may be selected from amines such as pyridine, triethylamine, diisopropylethylamine, 4-dimethylaminopyridine, imidazole, and ammonia; metal alkoxides such as sodium methoxide, sodium ethoxide, and potassium t-butoxide; carbonates such as sodium carbonate, potassium carbonate, and cesium carbonate; hydroxides such as sodium hydroxide, potassium hydroxide, and tetramethylammonium hydroxide, basic resins such as an anion exchange resin, solely or in combination, depending on reaction conditions. The amount of the base to be used is preferably 1 to 10 mol, particularly 1 to 2 mol per 1 mol of the used acid catalyst. After terminating the reaction, the reaction mixture may be used in a subsequent step (B) as it is or after filtration or condensation.

<Step (B)>

Then, in a metal removing step, the metal impurities are removed from the sugar-alcohol compound having the hydroxyl group protected with the protecting group in the step (A) (step (B)). The metal removing method in the step (B) is preferably, but not particularly limited to, (B1) liquid-liquid separation and water washing, (B2) distillation, or a combination thereof.

In the step (B), when (B1) liquid-liquid separation and water washing is performed, the reaction mixture obtained in the step (A) is desirably diluted with a separation solvent and subjected to liquid-liquid separation and water washing with deionized water more than once. The separation solvent to be used may be selected from hydrocarbons such as hexane, heptane, benzene, toluene, and xylene; ethers such as diethyl ether, dibutyl ether, and tetrahydrofuran; chlorinated solvents such as methylene chloride, chloroform, and 1,2-dichloroethane; esters such as ethyl acetate and butyl acetate; and ketones such as 2-butanone and 4-methyl-2-pentanone, solely or in combination. After the liquid-liquid separation and water washing, the solvent and the like are distilled off by condensation to obtain a sugar-alcohol compound having reduced metal impurities (i.e. the metal is removed) and protected with the protecting group.

In the step (B), when (B2) distillation is performed, the reaction mixture obtained in the step (A) or the sugar-alcohol compound having reduced metal impurities and protected with the protecting group obtained through (B1) liquid-liquid separation and water washing is desirably subjected to distillation under reduced pressure. The distillation method may be a usual method such as batch distillation or successive distillation. The pressure degree and the distillation temperature are selected depending on the boiling point of the target product. For example, the pressure degree is preferably determined such that the distillation temperature is 200° C. or lower, preferably 150° C. or lower. By the distillation, the sugar-alcohol compound from which the metal is removed can be obtained.

<Step (C)>

After the step (B), in a deprotecting step, the protecting group of the sugar-alcohol compound from which the metal has been removed is eliminated (step (C)). The deprotecting method in the step (C) is not particularly limited, and an appropriate method is desirably selected depending on the used protecting group. In view of prevention of metal impurity contamination, the step (C) is preferably performed by hydrolysis reaction or alcoholysis reaction.

Hereinafter, the case where deprotection (deprotection reaction) is performed by hydrolysis reaction or alcoholysis reaction on the sugar-alcohol compound having the hydroxyl group protected with acetonide (the acetonide protector) in the step (C) will be described in detail, but the present invention is not limited thereto. The deprotection reaction can be shown by the following partial formula. The deprotection reaction of the acetonide protector can be performed by reacting the acetonide protector with water or alcohol without a catalyst or in the presence of an acid catalyst, in a solvent or without a solvent. This reaction eliminates the acetonide and changes the group shown by the following partial formula (2) to the group shown by the following partial formula (1), thereby providing the sugar-alcohol compound from which the acetonide is eliminated.

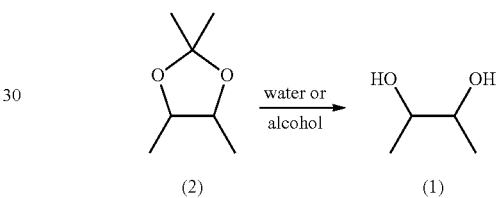

wherein the dotted line represents a bond.

When an acid catalyst is used, the acid catalyst may be selected from, for example, mineral acids such as sulfuric acid, hydrochloric acid, and nitric acid; Lewis acids such as boron trifluoride and boron trifluoride diethyl ether complex; sulfonic acids such as methanesulfonic acid and p-toluenesulfonic acid; salts such as pyridinium p-toluenesulfonate; carboxylic acids such as acetic acid, formic acid, oxalic acid, trifluoroacetic acid, and maleic acid; and acidic resins such as a cation exchange resin, solely or in combination, depending on reaction conditions. Among them, mineral acids and carbonic acids, low metal materials of which are easily available, are particularly preferable. The amount of the acid catalyst to be used is preferably 0.00001 to 10 mol, particularly 0.0001 to 5 mol, per 1 mol of the acetonide protector.

When the reaction is performed in a solvent, the reaction solvent may be selected from hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform, and 1,2-dichloroethane; non-protic polar solvents such as N,N-dimethylformamide, N,N-dimethylacetamide, dimethylsulfoxide, and N-methylpyrrolidone; esters such as ethyl acetate and butyl acetate; ketones such as acetone and 2-butanone; and nitriles such as acetonitrile, solely or in combination, depending on reaction conditions. In particular, water and alcohols, which are a reacting agent described later, are preferably used solely or in combination as the solvent.

As the water or alcohol to be reacted, deionized water, electronic industrial methanol, or electronic industrial ethanol is preferably used solely or in combination. In particular, deionized water is preferable. The amount of the water or alcohol to be used is preferably 1 to 1,000 mol, particularly 5 to 200 mol, per 1 mol of the acetonide protector.

The reaction temperature is preferably selected in the range of 0° C. to the reflux temperature of the solvent, depending on the reaction rate. To accelerate the reaction, acetone and so on generated by the deprotection reaction may be distilled off by heating under reduced pressure during the reaction.

In view of improvement of yield and purification of the target product, the reaction is desirably performed until completion of the reaction on trace of the reaction by gas chromatography (GC), liquid chromatography (LC), thin layer chromatography (TLC), or the like; in general, the reaction time is about 1 to 100 hours. After the completion of reaction, a solution of the sugar-alcohol compound from which the protecting group is eliminated is obtained. Then, if necessary, deionized water or a solvent may be added, and the concentration may be adjusted by condensation to finally obtain, preserve, and use a sugar-alcohol compound solution containing a desired solvent.

By the above-described method, the metal of the sugar-alcohol compound can be reduced. The sugar-alcohol compound in which the metal is reduced by the above metal reducing method has a solid content of every metal impurity including sodium of 100 ppb or less. Thus, the obtained sugar-alcohol compound with reduced metal can be suitably used in the semiconductor apparatus manufacturing process.

EXAMPLES

Hereinafter, the present invention will be specifically described with reference to examples and comparative examples, but the present invention is not restricted thereto.

[Example 1] Metal Reduction of Xylitol

A metal of xylitol was reduced by the inventive method for reducing a metal of a sugar-alcohol compound. First, a mixture of 152 g of xylitol, 312 g of 2,2-dimethoxypropane, 1.9 g of p-toluenesulfonic acid, and 450 g of toluene was refluxed for 16 hours by heating while gradually distilling off methanol generated by the reaction (step (A)). After cooling to room temperature, 1.2 g of 28% ammonia water was added to terminate the reaction. Then, liquid-liquid separation and water washing was performed with 150 g of deionized water 4 times (step (B)), and the solution was condensed under reduced pressure to obtain xylitol protected with acetonide as the product.

The obtained product was mixed with 600 g of deionized water and refluxed by heating while gradually distilling off acetone generated by the reaction. This reaction was continued until the reflux temperature was stabilized at 100° C. (step (C)). The reaction solution was cooled to room temperature, and 500 g of a xylitol aqueous solution was obtained.

The obtained xylitol aqueous solution had a concentration of 24.4 mass % as determined by non-volatile content measurement (at 160° C. for 1 hour), with a yield of 80%. The LC purity of the deprotected xylitol was 99.0%, and the sodium content thereof was 40 ppb with respect to xylitol as measured by ICP-MS.

[Comparative Example 1] Metal Content of Commercially Available Xylitol

The sodium content of xylitol available from Tokyo Chemical Industry Co., Ltd., was 3,500 ppb as measured by ICP-MS.

The xylitol of Example 1, in which the metal was reduced by the inventive method for reducing a metal of a sugar-alcohol compound, had a sodium content of 100 ppb or less, and thus had a significantly low sodium content compared with the commercially available xylitol of Comparative example 1.

[Example 2] Metal Reduction of Sorbitol

A metal of sorbitol was reduced by the inventive method for reducing a metal of a sugar-alcohol compound. First, a mixture of 1,000 g of sorbitol, 9 L of acetone, and 23 g of a cation exchange resin Amberlyst (registered trademark) 15 was stirred at 50° C. for 6 hours (step (A)). After cooling to room temperature, 17 g of triethylamine was added to terminate the reaction. The solid was collected by filtration and then condensed under reduced pressure to obtain 1,532 g of a crude product. Distillation was then performed under reduced pressure (step (B)) to obtain 1,180 g of sorbitol protected with acetonide.

To the sorbitol protected with acetonide was added a mixture of 0.6 g of electronic industrial nitric acid and 3,000 g of deionized water, and the solution was stirred under heating at 50° C. until the reaction solution was made homogeneous. Then, the pressure was gradually reduced while heating, and acetone generated by the reaction was gradually distilled off (step (C)). After the acetone was completely distilled off, the reaction solution was cooled to room temperature, and 2,749 g of a sorbitol aqueous solution was obtained.

The obtained sorbitol aqueous solution had a concentration of 25.8 mass % as determined by non-volatile content measurement (at 160° C. for 1 hour) and had a yield of 71%. The LC purity of the deprotected sorbitol was 99.6%, and the sodium content thereof was 20 ppb with respect to sorbitol as measured by ICP-MS.

[Comparative Example 2-1] Metal Content of Commercially Available Sorbitol

The sodium content of sorbitol available from Tokyo Chemical Industry Co., Ltd., was 4,000 ppb as measured by ICP-MS.

[Comparative Example 2-2] Recrystallization Purification of Sorbitol (1)

A mixture of 303 g of sorbitol and 1,860 g of methanol was stirred and dissolved at 70° C. The mixture was cooled to room temperature and then cooled in an ice-bath to obtain a solid of sorbitol. After the solid was collected by filtration, 800 g of methanol was added thereto, and the solution was stirred for 1 hour. The solid was then collected by filtration again, and dried at 60° C. under reduced pressure. 191 g of the solid of sorbitol was thus obtained with a yield of 63%. The sodium content thereof was 4,000 ppb as measured by ICP-MS.

[Comparative Example 2-3] Recrystallization Purification of Sorbitol (2)

A mixture of 300 g of sorbitol, 1,200 g of methanol, and 150 g of deionized water was stirred and dissolved at 80° C. The mixture was cooled to room temperature and then cooled in an ice-bath to obtain a solid of sorbitol. After the solid was collected by filtration, 600 g of methanol was added thereto, and the solution was stirred for 1 hour. The solid was then collected by filtration again, and dried at 60° C. under reduced pressure. 136 g of the solid of sorbitol was thus obtained with a yield of 45%. The sodium content thereof was 3,500 ppb as measured by ICP-MS.

[Comparative Example 2-4] Recrystallization Purification of Sorbitol (3)

A mixture of 103 g of sorbitol, 500 g of methanol, 10 g of deionized water, and 0.05 g of 24 mass % maleic acid aqueous solution was stirred and dissolved at 75° C. The mixture was cooled to room temperature and then cooled in an ice-bath to obtain a solid of sorbitol. After the solid was collected by filtration, 350 g of methanol was added thereto, and the solution was stirred for 1 hour. The solid was then collected by filtration again, and deionized water was added to obtain 500 g of a sorbitol aqueous solution. The obtained sorbitol aqueous solution had a concentration of 10.9 mass % as determined by non-volatile content measurement (at 160° C. for 1 hour) and had a yield of 90%. The sodium content thereof was 510 ppb with respect to sorbitol as measured by ICP-MS.

The sorbitol of Example 2, in which the metal was reduced by the inventive method for reducing a metal of a sugar-alcohol compound, had a sodium content of 100 ppb or less, and thus had a significantly low sodium content compared with the commercially available sorbitol of Comparative example 2-1 and the sorbitol of Comparative examples 2-2 to 2-4, in which the metal was reduced without protecting hydroxyl groups of sorbitol.

The above results demonstrated that the inventive method for reducing a metal of a sugar-alcohol compound could easily prepare a large amount of the sugar-alcohol compound with reduced metal. In addition, the inventive sugar-alcohol compound, in which the metal is reduced, can be suitably used in, for example, the semiconductor manufacturing process requiring low metal content. This indicates that the present invention has high industrial value.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A method for reducing a content of metal impurities of a sugar-alcohol compound, the method comprising the steps of:
   (A) protecting a hydroxyl group of a sugar-alcohol compound containing metal impurities with a protecting group;
   (B) removing the metal impurities from the sugar-alcohol compound having the hydroxyl group protected with the protecting group; and
   (C) eliminating the protecting group of the sugar-alcohol compound from which the metal has been removed, wherein
   step (C) is performed by a hydrolysis reaction using deionized water.

2. The method according to claim 1, wherein the sugar-alcohol compound containing metal impurities is selected from the group consisting of erythritol, threitol, arabinitol, xylitol, ribitol, iditol, galactitol, sorbitol, mannitol, volemitol, perseitol, octitol, inositol, and quercitol.

3. The method according to claim 1, wherein the step (B) includes (B1) liquid-liquid separation and water washing or (B2) distillation.

4. The method according to claim 2, wherein the step (B) includes (B1) liquid-liquid separation and water washing or (B2) distillation.

5. The method according to claim 1, wherein the protecting group is acetonide.

6. The method according to claim 2, wherein the protecting group is acetonide.

7. The method according to claim 3, wherein the protecting group is acetonide.

8. The method according to claim 4, wherein the protecting group is acetonide.

9. The method according to claim 1, wherein the sugar-alcohol compound obtained by the method has a sodium impurity content of 100 ppb or less.

10. The method according to claim 9, wherein the sodium impurity content is 50 ppb or less.

11. The method according to claim 1, wherein the deionized water is used in the presence of an acid catalyst.

12. The method according to claim 11, wherein the acid catalyst is a mineral acid or a carbonic acid.

* * * * *